United States Patent
Levis et al.

(10) Patent No.: US 10,398,300 B2
(45) Date of Patent: Sep. 3, 2019

(54) INTRAOCULAR LENS ALIGNMENT

(71) Applicant: ALCON RESEARCH, LTD., Fort Worth, TX (US)

(72) Inventors: Ilias Levis, Westwood, MA (US); Katariina Lahti, Westwood, MA (US); Boris Nalibotski, New London, CT (US)

(73) Assignee: Alcon Research, Ltd., Fort Worth, TX (US)

(*) Notice: Subject to any disclaimer, the term of this patent is extended or adjusted under 35 U.S.C. 154(b) by 446 days.

(21) Appl. No.: 14/813,873

(22) Filed: Jul. 30, 2015

(65) Prior Publication Data

US 2015/0335474 A1 Nov. 26, 2015

Related U.S. Application Data

(63) Continuation of application No. 12/705,799, filed on Feb. 15, 2010, now Pat. No. 9,119,565.

(60) Provisional application No. 61/153,709, filed on Feb. 19, 2009, provisional application No. 61/155,562, filed on Feb. 26, 2009.

(51) Int. Cl.
  *A61B 3/00* (2006.01)
  *A61F 9/00* (2006.01)
  *A61F 9/007* (2006.01)
  *A61F 2/16* (2006.01)

(52) U.S. Cl.
  CPC .......... *A61B 3/0025* (2013.01); *A61B 3/0041* (2013.01); *A61B 3/0058* (2013.01); *A61F 2/16* (2013.01); *A61F 2/1662* (2013.01); *A61F 9/007* (2013.01); *A61F 9/0017* (2013.01); *A61F 2/1645* (2015.04); *A61F 9/0008* (2013.01)

(58) Field of Classification Search
  CPC ............................ A61F 2/1662; A61F 9/0017
  USPC ........................................................ 606/107
  See application file for complete search history.

(56) References Cited

U.S. PATENT DOCUMENTS

| | | | |
|---|---|---|---|
| 5,089,022 A | 2/1992 | Koester et al. |
| 5,740,802 A | 4/1998 | Nafis et al. |
| 5,740,803 A | 4/1998 | Gray et al. |
| 5,757,461 A | 5/1998 | Kasahara et al. |
| 5,867,210 A | 2/1999 | Rod |
| 5,975,084 A | 11/1999 | Alpins |

(Continued)

FOREIGN PATENT DOCUMENTS

| | | |
|---|---|---|
| EP | 1316287 A2 | 6/2003 |
| JP | 2004081830 A | 3/2004 |

(Continued)

OTHER PUBLICATIONS

Arbelaez et al, "Clinical Outcomes of Corneal Vertex Versus Central Pupil References with Aberration-Free Ablation Strategies and Lasik," Inv. Ophthal. & Vis. Science, Dec. 2008 vol. 49, NR. 12; pp. 5287-5294. ISSN: 1552-5783.

(Continued)

*Primary Examiner* — Zachary W Wilkes

(57) ABSTRACT

A method for generating a radial alignment guide for an eye includes collecting preoperative alignment data relative to a pupil from an eye that is not dilated. The method also includes locating a pupil center of the eye while dilated. The method further includes displaying the alignment data on an image of the dilated eye relative to the pupil center. In particular embodiments, software embodied in a computer-readable medium is executable by a processor to perform the steps of such a method.

15 Claims, 4 Drawing Sheets

(56) References Cited

U.S. PATENT DOCUMENTS

| | | |
|---|---|---|
| 6,241,356 B1 | 6/2001 | Von Wallfeld et al. |
| 6,352,519 B1 | 3/2002 | Anis et al. |
| 7,146,983 B1 | 12/2006 | Hohla et al. |
| 7,331,667 B2 | 2/2008 | Grotehusmann et al. |
| 7,654,668 B2 | 2/2010 | Neuhann et al. |
| 8,414,123 B2 | 4/2013 | Boukhny et al. |
| 8,486,085 B2 | 7/2013 | Moeller et al. |
| 2002/0097378 A1 | 7/2002 | Saito et al. |
| 2003/0053025 A1 | 3/2003 | Turner et al. |
| 2003/0060880 A1 | 3/2003 | Feingold |
| 2003/0071893 A1 | 4/2003 | Miller et al. |
| 2003/0120266 A1 | 6/2003 | Fujieda |
| 2004/0100619 A1 | 5/2004 | Oliver et al. |
| 2004/0102799 A1 | 5/2004 | Perez et al. |
| 2004/0169817 A1 | 9/2004 | Grotehusmann et al. |
| 2005/0025365 A1 | 2/2005 | Oosawa et al. |
| 2005/0117118 A1 | 6/2005 | Miller et al. |
| 2005/0225721 A1 | 10/2005 | Harris et al. |
| 2006/0247659 A1 | 11/2006 | Moeller et al. |
| 2007/0055222 A1 | 3/2007 | Hohla et al. |
| 2007/0274626 A1 | 11/2007 | Sabeta |
| 2008/0247616 A1 | 10/2008 | Pescatore et al. |
| 2009/0137988 A1 | 5/2009 | Kurtz |

FOREIGN PATENT DOCUMENTS

| | | |
|---|---|---|
| JP | 2006136714 A | 6/2006 |
| RU | 2209053 C2 | 7/2003 |
| WO | 9203989 A1 | 3/1992 |
| WO | 0128476 A1 | 4/2001 |
| WO | 0178584 A2 | 10/2001 |
| WO | 0189373 A2 | 11/2001 |
| WO | 2002064031 A2 | 8/2002 |
| WO | 02074248 A2 | 9/2002 |
| WO | 03022137 A2 | 3/2003 |
| WO | 2006044056 A2 | 4/2006 |
| WO | 2008008044 A2 | 1/2008 |

OTHER PUBLICATIONS

Ma et al, "Simple Method for Accurate Alignment in Toric Phakic and Aphakic Intraocular Lens Implantation," J. Cataract & Refr Surg, Oct. 2008, vol. 34, No. 10, pp. 1631-1636, ISSN: 0886-3350.

Nguyen et al, "Digital Overlay Technique for Documenting Toric Intraocular Lens Axis Orientation," J. of Cataract & Refr Surg, Oct. 2000, vol. 26, NR. 10, pp. 1496-1504, ISSN: 0886-3350.

Yang et al, "Pupil Location Under Mesopic, Photopic, and Pharmacalogically Dilated Conditions," Inv. Ophthal. & Vis Science, Jul. 2002, vol. 43, No. 7, pp. 2509-2512, ISSN: 0146-0404.

PCT/US2010/024482, International Search Report, International Searching Authority, dated Jun. 15, 2010, 4 pgs.

PCT/US2010/024483, International Search Report, International Searching Authority, dated Jun. 15, 2010, 4 pgs.

Kent, "Locking on: Eye Tracking for the 21st Century," Rev. of Ophthal. Jul. 2007, 7 pgs.

INTRAOCULAR LENS ALIGNMENT

RELATED APPLICATIONS

This application is a continuation of U.S. application Ser. No. 12/705,799 filed on Feb. 15, 2010 which claims priority to U.S. Provisional Application Ser. No. 61/155,562 filed on Feb. 26, 2009 and U.S. Provisional Application Ser. No. 61/153,709 filed on Feb. 19, 2009, each of which are hereby fully incorporated herein by reference.

BACKGROUND

For the past decade, ophthalmic surgeons have tried several methods to correct preexisting astigmatism during cataract eye surgery, including making incisions into the cornea to alter the shape of the eye. Now due to the unique design of toric intraocular lenses (IOL), astigmatism can be reduced or corrected without further surgical intervention. A toric IOL restores focus to the eye when the natural lens or cataract is removed, but it is also designed to correct preexisting astigmatism using the same technology that has been successfully used in contact lenses.

Before the surgery, the amount of corneal astigmatism that needs to be corrected must be determined. In general, the procedure is as follows:
1. Pre-Operative Examination (Keratometry, Corneal Topography, Slit Lamp)
2. Calculation of IOL orientation
3. IOL Selection
4. Surgical insertion of toric IOL and alignment according to pre-calculated axis The success of such procedures depends in part upon the angular accuracy of the IOL alignment. All of the above steps have the potential to introduce a certain degree of error resulting in under-correction of astigmatism. However, a dominant source of error is the misalignment of the toric IOL according to the calculated angular value after it is inserted into the anterior chamber of a patient's eye during the cataract procedure. This may be, for example, due to the fact that the calculated IOL angle is based on measurements conducted with the patient sitting upright (pre-op setup) and alert, while during surgery the patient is in the supine position where cyclorotation occurs and under the influence of local anesthetic. Each degree of angular error may cause a 3.3% loss of astigmatic correction by the toric IOL. Thus 10° of error may cause a 33% reduction in the effect of the toric IOL, which is equivalent to using a spherical lens without astigmatism correction.

In order to avoid error due to the cyclorotation effect, there are currently several techniques to mark the eye with the meridian and pre-calculated IOL axis of alignment during the pre-operative examination. These techniques typically require the surgeon to place reference marks at the 3-o'clock and 9-o'clock meridians at the limbus utilizing markers or puncturing devices. Markings made by markers may be inaccurate, and may wash away or drift. Furthermore, puncturing the cornea is invasive and carries considerable risk of infection and/or other side effects.

SUMMARY

In certain embodiments of the present invention, a method for generating a radial alignment guide for an eye includes collecting preoperative alignment data relative to a pupil from an eye that is not dilated. The method also includes locating a pupil center of the eye while dilated. The method further includes displaying the alignment data on an image of the dilated eye relative to the pupil center. In particular embodiments, software embodied in a computer-readable medium is executable by a processor to perform the steps of such a method.

In other embodiments, a system for generating a radial alignment guide for an eye includes a memory, a processor, and a display. The memory is operable to store preoperative alignment data relative to a pupil from an eye that is not dilated. The processor is operable to locate a pupil center of the eye while dilated. The display is operable to display the alignment data on an image of the dilated eye relative to the pupil center.

BRIEF DESCRIPTION OF THE DRAWINGS

The present invention may be understood with reference to the following drawings wherein.

DETAILED DESCRIPTION

In various embodiments of the present invention, toric intraocular lens alignment (IOL) for cataract surgery is improved by providing an accurate radial grid or alignment guide to assist a surgeon in lens placement. A slit lamp microscope may be used to obtain images of an eye, and an image overlay including a radial grid, lens alignment guide, and/or other fiducials for rotational alignment may be provided as a surgical guide in any suitable form including a computer display, a printed image of the eye showing information, or by direct projection onto the eye during the procedure.

According to various methods and systems described herein, a radial grid is centered on a center of the pupil and overlaid on an image of the eye (or in one embodiment directly onto the eye). The pupil center may be located, e.g., automatically using any appropriate center-finding image processing technique, or manually through a point-and-click computer interface or the like. For example, the pupil center can be located using a variety of image analysis techniques, including but not limited to the techniques described in U.S. Pat. No. 5,740,803 to Gray et al., which is incorporated herein by reference. The grid may include vertical and horizontal meridians and a scale at any suitable degree of accuracy. Within a user interface, angular measurements may be selected and marked on the grid to various features of the eye such as blood vessels, iris features, or any other appropriate fiducials. The grid may also include an alignment guide showing the correct rotational orientation for an IOL lens, as calculated prior to a surgical procedure. By calculating an angle relative to, e.g., the vertical meridian, an accurate guide may be displayed in the radial grid for use by a surgeon.

Figure 1:
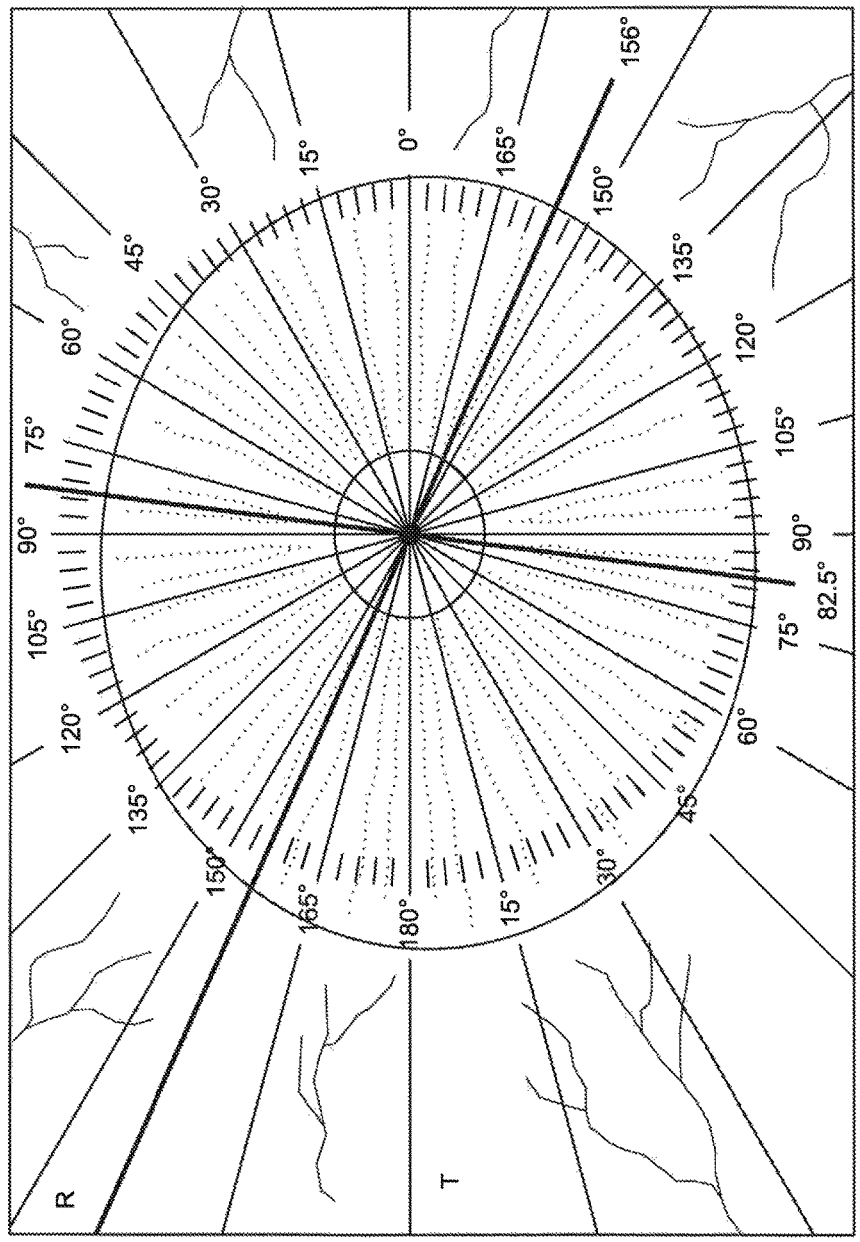
FIG. 1 shows an image of an eye with a radial overlay according to a particular embodiment of the present invention.

FIG. 1 shows an image of an eye with a radial overlay. As depicted, a horizontal meridian passes through 0 degrees and 180 degrees, and a vertical meridian passes through plus and minus 90 degrees. An angle of 82.5 degrees has been marked as a reference angle to some eye feature selected by a surgeon or the like, and an angle of 156 degrees is depicted for use in aligning a toric intraocular lens (also referred to generally herein as a lens.

Other aspects of systems and methods for aligning a lens are described below. In an embodiment using a slit lamp microscope, a suitable video camera may be mounted on a slit lamp microscope through a beam splitter. The camera may be connected to a computer with image acquisition hardware using a connector such as USB, FireWire or GigE port. Live display may be started, and the camera may be aligned so that the horizontal axis of the camera's field of view is aligned with the horizontal slit of the slit lamp. High quality images may be captured with the patient sitting upright, and software may attempt to automatically locate the central point of the pupil. The software may also include a manual pupil localization tool. Once the central point of the pupil is defined, the software may overlay a radial grid with its center located on that point as shown, e.g., in FIG. 1. The 0 to 180° axis of the radial will coincide with the 3- and 9-o'clock meridians of the eye since the camera is rotationally calibrated with the slit lamp. The software may also have the capability to provide the following:

Overlay of the toric IOL axis according to the angular value calculated through Keratometry. The toric axis IOL axis will cross the center of the dial and the angular value will be in reference to the 0 to 180° axis of the overlaid dial (see line with angle value 156 degrees in FIG. 1)

Overlay of axes that cross through the dial center and other anatomical landmarks that the surgeon chooses as fiducial marks on the eye's iris periphery or limbar vessels. The software will display the angular value next to each one of these reference points (see line with angle value 82.5 degrees in FIG. 1).

The software may also designate the images with the left or right eye designation and temporal or nasal side of the eye (see letters "R" and "T" in FIG. 1)

The processed images may be stored on the computer's hard drive, removable memory, or in the patient database of the medical facility. The surgeon may retrieve and display images with overlay in an operating room in a high quality photograph or on a monitor, or the overlay may be projected directly onto a patient's eye using an appropriate projector.

Figure 2:
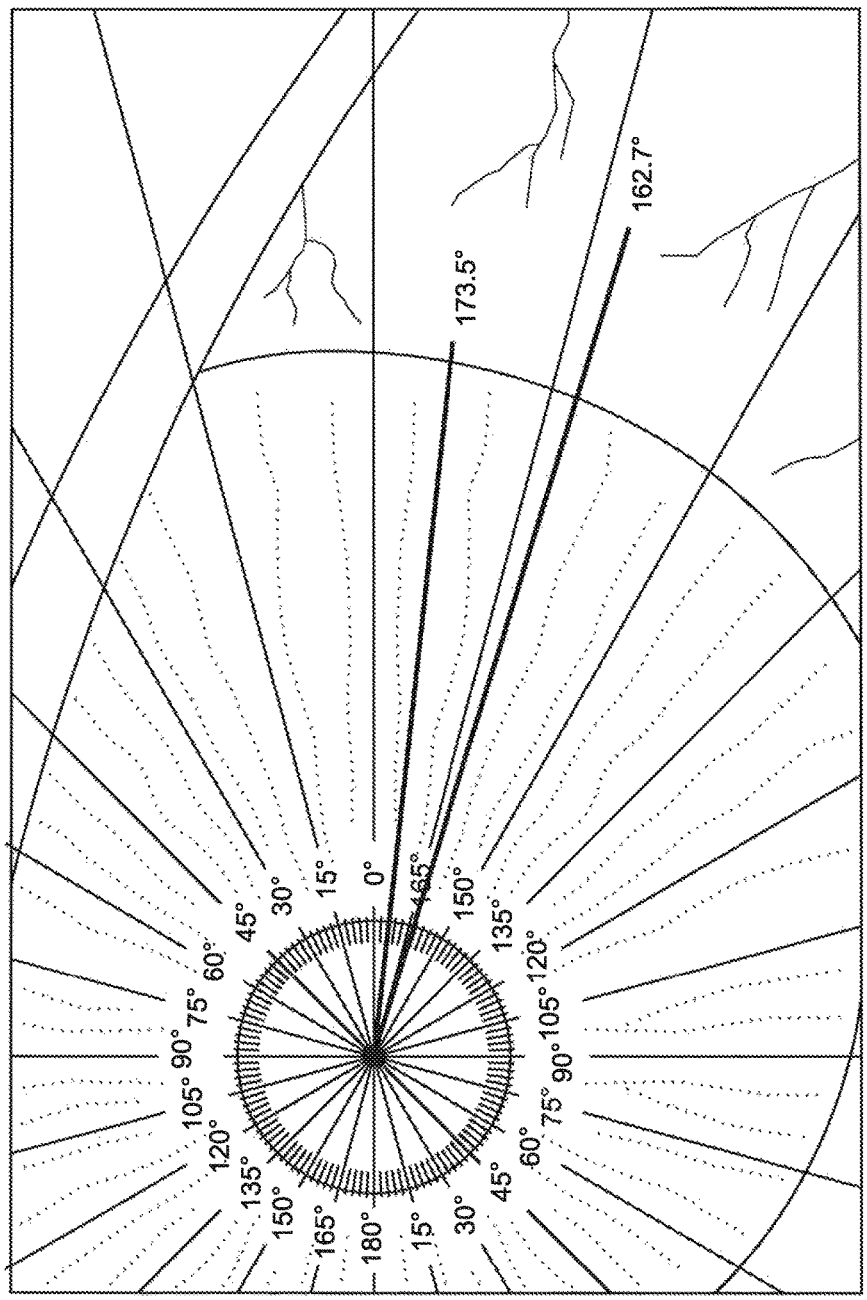
FIG. 2 shows an alternative configuration for a radial grid overlay, along with user-provided radial measurements, according to another embodiment of the present invention.
Figure 3:
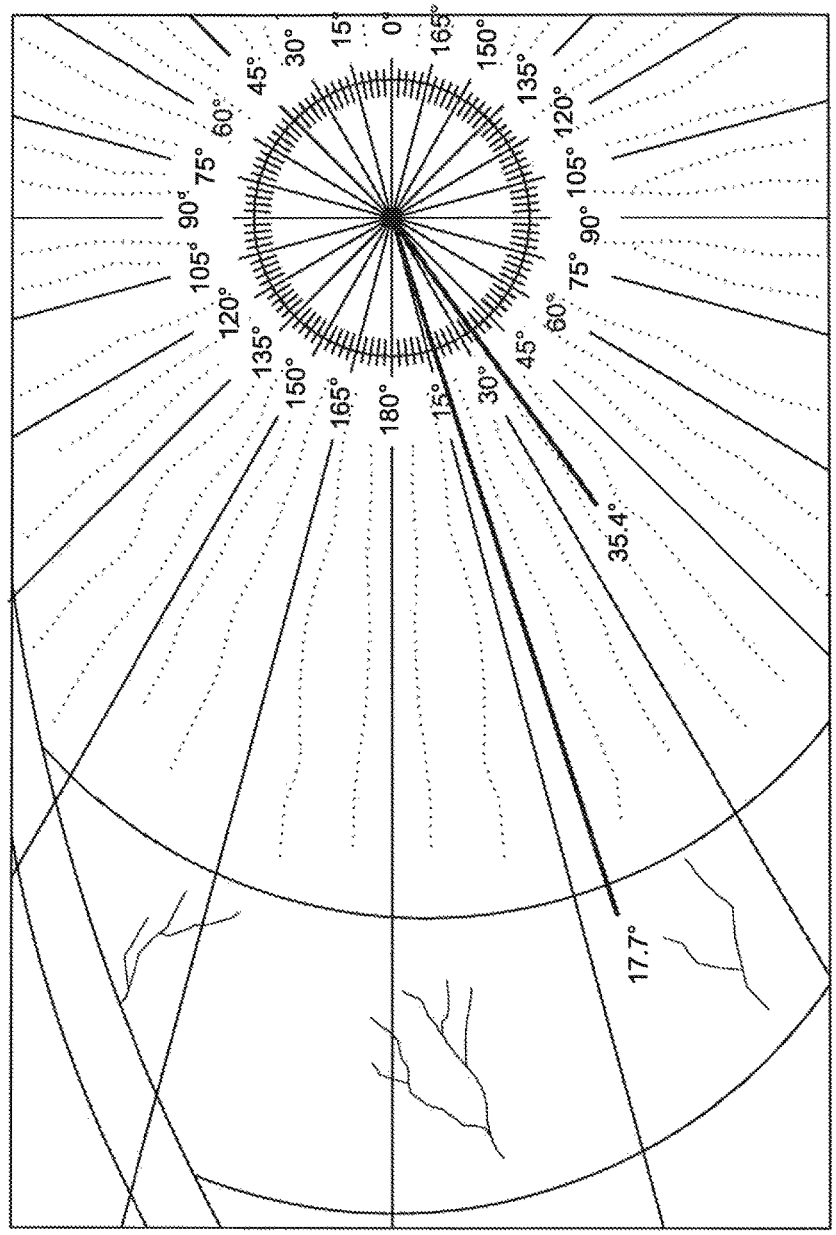
FIG. 3 shows an alternative configuration for a radial grid overlay, along with user-provided radial measurements according to another embodiment of the present invention.

Based on the overlaid axes of the fiducial points, the surgeon can accurately place a surgical protractor that determines toric IOL insertion regardless of the cyclorotation effect. As soon as the protractor is aligned with the actual eye meridians, the surgeon can proceed with aligning the toric IOL according to the calculated angular value. FIGS. 2 and 3 illustrate alternative arrangements for a radial overlay, along with user-provide measurements and/or lens alignment information.

Figure 4:
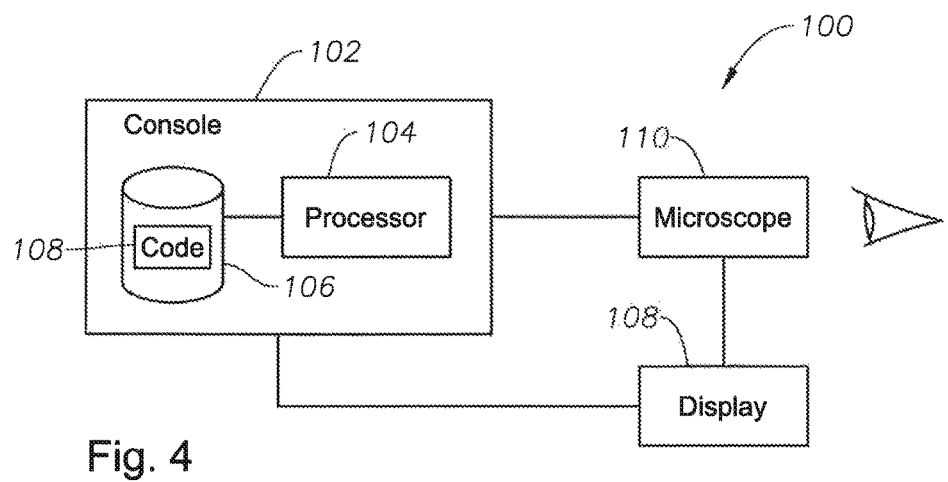
FIG. 4 is a block diagram of a surgical system according to a particular embodiment of the present invention.

This method addresses several sources of error in the IOL alignment process for cataract surgery by
 a. Providing a mechanism for accurate camera alignment with the slit lamp microscope
 b. Offering precise location of the pupil center based on image analysis
 c. Enabling accurate protractor placement during surgery by guiding the surgeon to place the protractor according to the actual meridians of the eye hence generating an accurate reference angular system The methods or processes described above, and steps thereof, may be realized in hardware, software, or any combination of these suitable for a particular application. FIG. 4 is a block diagram of a system 100 for generating a surgical display according to a particular embodiment of the present invention. The system 100 includes a console 102 having a processor 104. The processor 104 may be one or more microprocessors, microcontrollers, embedded microcontrollers, programmable digital signal processors or other programmable device, along with internal and/or external memory 106. The processor 104 may also, or instead, be embodied in an application specific integrated circuit, a programmable gate array, programmable array logic, or any other device or combination of devices that may be configured to process electronic signals. The memory 106 may be any suitable form of data storage, including electronic, magnetic, or optical memory, whether volatile or non-volatile, that includes code 108 comprising instructions executed by processor 104. It will further be appreciated that computer executable code 108 may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

In the embodiment depicted in FIG. 4, the system 100 also includes a display 108 and a microscope 110 for observing an eye during surgery. The display 108 may include any suitable output device for generating an alignment guide for the eye, including a printer, a video display, or a light projector. In particular embodiments, the display 108 may be coupled to the microscope 110 so that the image is projected into the view of the microscope. The microscope 110 may be any suitable tool for visually inspecting the eye, which may include electronic and/or optical views. Various other suitable components, including any of the examples described herein, may also be substituted for the components of system 100.

Figure 5:
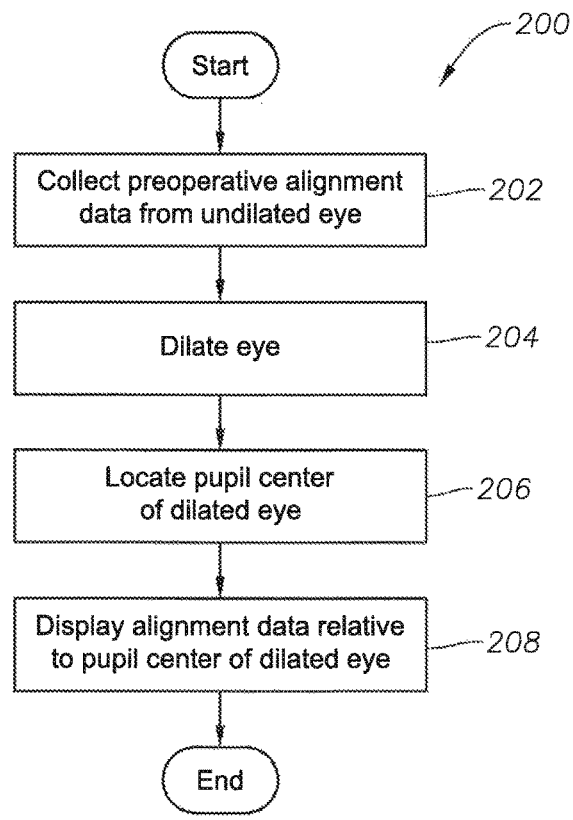
FIG. 5 is a flow chart illustrating an example method of generating a surgical display according to a particular embodiment of the present invention.

FIG. 5 is a flow chart 200 illustrating an example method for generating a surgical display including a radial alignment guide in accordance with a particular embodiment of the present invention. At step 202, preoperative alignment data relative to a pupil is collected from an eye that is not dilated. At step 204, the eye is dilated. At step 206, the pupil center is located. The pupil center can be located manually, such as by using a pointing device, or automatically, such as by image analysis software. At step 208, an alignment guide is displayed on an image of the dilated eye relative to the pupil center. The alignment guide can correspond to any of the various embodiments described herein.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art.

What is claimed is:

1. A method for generating a radial alignment guide, comprising:
    collecting preoperative data from a patient's eye while the patient is in a seated position, the preoperative data comprising:
        preoperative rotational alignment data for a toric intraocular lens (IOL), the preoperative rotational alignment data comprising a rotational offset relative to a meridian of the patient's eye;
        locations of one or more anatomical features on the patient's eye, the locations of the one or more anatomical features being determined based on a preoperative image of the patient's eye;
    generating an intraoperative image of the patient's eye while the patient is in a supine position;
    aligning an axis of an intraoperative radial grid with the meridian of the patient's eye based at least in part of the locations of the one or more anatomical features on the patient's eye; and
    displaying a rotational alignment axis for the toric IOL on the intraoperative image of the patient's eye, the rotational alignment axis being offset relative to the axis of the intraoperative radial grid by an amount equal to the rotational offset of the preoperative rotational alignment data.

2. The method of claim 1, further comprising displaying the axis of the intraoperative radial grid on the intraoperative image of the patient's eye.

3. The method of claim 1, wherein the anatomical features of the patient's eye comprise one or more of blood vessels and iris features.

4. The method of claim 1, wherein aligning an axis of an intraoperative radial grid with the meridian of the patient's eye comprises, at least in part, registering the preoperative image of the patient's eye with the intraoperative image of the patient's eye.

5. The method of claim 1, wherein displaying the rotational alignment axis for the toric IOL on the intraoperative image of the patient's eye comprises projecting the rotational alignment axis into the view of a surgical microscope.

6. A system for generating a radial alignment guide, comprising:
    a memory operable to store preoperative data from a patient's eye, the preoperative data being collected while the patient is in a seated position, the preoperative data comprising:
        preoperative rotational alignment data for a toric intraocular lens (IOL), the preoperative rotational alignment data comprising a rotational offset relative to a meridian of the patient's eye;
        locations of one or more anatomical features on the patient's eye, the locations of the one or more anatomical features being determined based on a preoperative image of the patient's eye;
    an imaging device operable to generate an intraoperative image of the patient's eye while the patient is in a supine position;
    a processor operable to align an axis of an intraoperative radial grid with the meridian of the patient's eye based at least in part of the locations of the one or more anatomical features on the patient's eye; and
    a display device operable to display a rotational alignment axis for the toric IOL on the intraoperative image of the patient's eye, the rotational alignment axis being offset relative to the axis of the intraoperative radial grid by an amount equal to the rotational offset of the preoperative rotational alignment data.

7. The system of claim 6, wherein the display device is further operable to display the axis of the intraoperative radial grid on the intraoperative image of the patient's eye.

8. The system of claim 6, wherein the anatomical features of the patient's eye comprise one or more of blood vessels and iris features.

9. The system of claim 6, wherein aligning an axis of an intraoperative radial grid with the meridian of the patient's eye comprises, at least in part, registering the preoperative image of the patient's eye with the intraoperative image of the patient's eye.

10. The system of claim 6, wherein the display device comprises a projector operable to project the rotational alignment axis into the view of a surgical microscope.

11. Software embodied in a non-transitory computer-readable medium, the software operable, when executed by a processor, to perform the steps of:
    collecting preoperative data from a patient's eye while the patient is in a seated position, the preoperative data comprising:
        preoperative rotational alignment data for a toric intraocular lens (IOL), the preoperative rotational alignment data comprising a rotational offset relative to a meridian of the patient's eye;
        locations of one or more anatomical features on the patient's eye, the locations of the one or more anatomical features being determined based on a preoperative image of the patient's eye;
    generating an intraoperative image of the patient's eye while the patient is in a supine position;
    aligning an axis of an intraoperative radial grid with the meridian of the patient's eye based at least in part of the locations of the one or more anatomical features on the patient's eye; and
    displaying a rotational alignment axis for the toric IOL on the intraoperative image of the patient's eye, the rotational alignment axis being offset relative to the axis of the intraoperative radial grid by an amount equal to the rotational offset of the preoperative rotational alignment data.

12. The software of claim 11, wherein the software is further operable to display the axis of the intraoperative radial grid on the intraoperative image of the patient's eye.

13. The software of claim 11, wherein the anatomical features of the patient's eye comprise one or more of blood vessels and iris features.

14. The software of claim 11, wherein aligning an axis of an intraoperative radial grid with the meridian of the patient's eye comprises, at least in part, registering the preoperative image of the patient's eye with the intraoperative image of the patient's eye.

15. The software of claim 11, wherein displaying the rotational alignment axis for the toric IOL on the intraoperative image of the patient's eye comprises projecting the rotational alignment axis into the view of a surgical microscope.

* * * * *